United States Patent [19] [11] Patent Number: 4,905,671
Senge et al. [45] Date of Patent: Mar. 6, 1990

[54] INDUCEMENT OF BONE GROWTH BY ACOUSTIC SHOCK WAVES

[75] Inventors: Theodor A. Senge, Castrop-Rauxel; Klaus-Dieter Richter, Havixbeck; Werner Schwarze, Stockach, all of Fed. Rep. of Germany

[73] Assignee: Dornier Medizintechnik Gmbh, Fed. Rep. of Germany

[21] Appl. No.: 142,124

[22] Filed: Jan. 11, 1988

[51] Int. Cl.⁴ .............................................. A61F 5/00
[52] U.S. Cl. ................................ 128/24 A; 128/419 F
[58] Field of Search ........................ 128/419 F, 24 A

[56] References Cited

U.S. PATENT DOCUMENTS 4,530,360  7/1985  Duarte ............................ 128/419 F
4,619,264 10/1986  Singh ............................. 128/419 F
4,683,873  8/1987  Cadossi et al. .................. 128/419 F Primary Examiner—Ruth S. Smith
Attorney, Agent, or Firm—Burns, Doane, Swecker & Mathis

[57] ABSTRACT

A method of inducing bone growth which comprises directing energy in the form of acoustic shock waves to a site where bone growth is desired, the amount of energy applied being sufficient to produce bleeding.

10 Claims, 2 Drawing Sheets

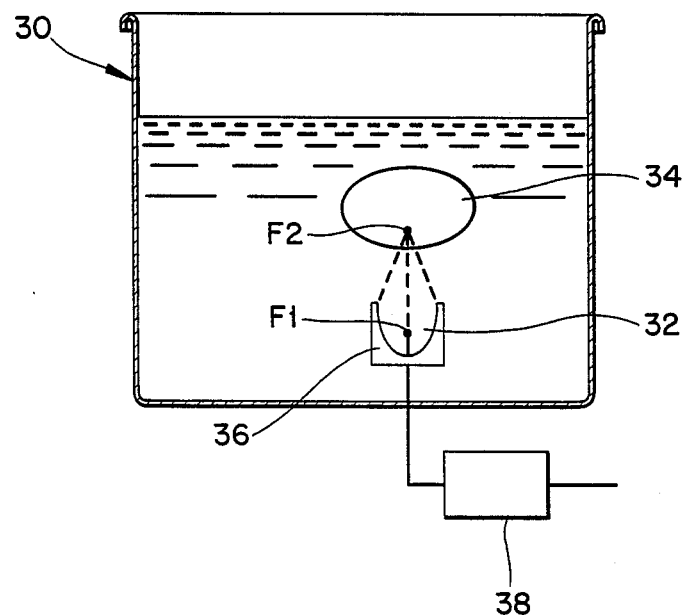

INDUCEMENT OF BONE GROWTH BY ACOUSTIC SHOCK WAVES

BACKGROUND OF THE INVENTION

The present invention relates to the healing of bone fractures, non-unions, and pseudoarthroses, and to the induction of an increase in bone mass.

Bones are important organs of the human body. On the one hand, they act as supports, and on the other hand, they serve as a storage facility for calcium and phosphorus. These two elements are present in bone in the form of apatite, a mineral. Depending upon other conditions in the body, calcium and phosphorus may be introduced or removed by hormonal regulation. For example, the body keeps a relatively constant level of calcium in the blood, because important biological activities such as contraction of muscles, beating of the heart, and clotting of blood require quite constant blood levels of calcium.

When the blood calcium level drops, more calcium is taken out of the bones to maintain the appropriate level. When the blood calcium returns to normal, increased amounts of calcium are no longer taken from the bones.

Living bone contains a protein framework (the osteoid matrix) in which the calcium salts are deposited. Bone, like many other tissues of the body, is constantly rebuilt or remodeled. Old bone is torn down, resorbed and replaced with new bone. The cells affecting the removal of calcium and phosphorus from bones are the osteoclasts. Those which deposit calcium and phosphorus in bone are osteoblasts. Thus, the building of bones by the osteoblasts takes place by the initial formation of the osteoid matrix which consists primarily of collagens (a fibrous protein) which is surrounded by proteoglycans and glycoproteins. Subsequent to formation, the matrix is enclosed by apatite to combine the desirable properties of the elastic fibers and the hard mineral substance.

As mentioned above, the osteoclasts are bone decomposing cells. They are generally multinuclear cells provided with numerous different enzyme activities. The enzymes and the acidity of the osteoclasts facilitate the decomposition of bone by on the one hand, dissolving the mineral thereby releasing ionic calcium and phosphate, and on the other, decomposing the organic matrix.

In intact, healthy bones, osteoblasts and osteoclasts coexist and both are active. This means that in healthy bone, a dynamic equilibrium is present between the osteoclast activity (bone decomposition) and osteoblast activity (bone building). Thus, over time, the average bone mass remains constant. Interference with this equilibrium leads either to a decrease or increase in bone mass.

Disturbances in this equilibrium can either be localized (a fracture) or generalized (osteopathies) such as for example, osteoporosis, osteomalacia, hyperparathyroidism and Paget's disease.

When a bone is fractured, there is generally tearing of small blood vessels causing bleeding at the fracture site. Bleeding occurs between the bone fragments and into the marrow cavity, as well as under the periosteum (the thin, tough fibrous membrane which covers the outer surface of the bone). This collection of blood and serum forms a clot which is called the "fracture-hematoma". The fracture-hematoma plays a very important role in fracture repair. The fracture-hematoma first undergoes a repair process which is similar to that which occurs in injuries of other tissues. This is known as organization of the clot. In the first few days there is rapid growth into the clot of cellular granulation tissue composed of fibroblasts and new fine capillary blood vessels. In about a week, small areas of young bone begin to be formed in an irregular pattern about these capillary blood vessels.

In addition to this organization of the clot by fibrous granulation tissue, there is a proliferation or multiplication of both osteoblasts and chondroblasts (cartilage-forming cells). Both new bone and new cartilage are laid down. This eventually forms the "callus", not only between the bone fragments but also under the periosteum and around the fracture site. At the same time that this new cartilage and new bone is being formed, all devitalized bone from the ends of the fracture fragments is being absorbed by osteoclasts, to be replaced by new bone.

The new cartilage which is formed in the callus is usually ultimately transformed into bone. Sometimes, however, cartilage formation predominates and little or no new bone is formed. This can happen when there is too much mobility between the fracture fragments. As a result, the fracture does not unite and a false joint (pseudoarthrosis) results. For this reason, immobilization of the fragments to prevent motion between them is essential during the healing stage of a fracture.

The primary callus which is first formed is fibrous at first and later becomes ossified. Primary boney callus is usually complete in some five to seven weeks after injury, but mineralization by deposit of calcium salts is not completed. It usually takes about two to four weeks longer, on the average, to complete mineralization so that the fracture fragments are united by solid bone. This time schedule varies for the different bones and can be much longer before bony union occurs. While this is referred to as "clinical union", this primary bone callus is a primitive type of solid bone and is actually only a temporary repair. Eventually, the adult type of lamellar bone must be formed in its place, and the original microscopic architecture of the bone must be restored.

Adult lamellar bone with its Haversian systems and medullary cavity forms very slowly. It requires for its formation the existing model of primitive new bone which the primary bony callus supplies. By the slow and continuous process of absorption and replacement, new adult bone is laid down in place of primary callus. Eventually, the parallel lamellar pattern of adult bone with its Haversian systems is restored and the marrow cavity which was temporarily occluded is recanalized. Excess callus is absorbed, thus restoring the original contour of the bone. It is only at this stage that anatomical healing is complete. This entire process takes a year or even longer for a major bone.

Unfortunately, various circumstances may interfere with fracture repair. One of the common interferences is loss of the fracture-hematoma. Since the fracture-hematoma plays the stellar role in the healing of a fracture, if this hematoma does not form, or is lost or escapes, the normal healing process is delayed or sometimes does not even occur. For example, this happens in compound fractures in which bleeding is to the outside and not within a closed space and thus no clot forms, and in surgical reduction of a fracture, for the same reason. This is one reason why closed reduction of a fracture is preferred if it is possible by this means to obtain and maintain good alignment and contact of the fracture fragments.

Because of the relatively long duration of impaired function resulting from a bone fracture, various methods have been suggested in the art for accellerating healing. For example, Duarte, U.S. Pat. No. 4,530,360, describes an apparatus and method for healing bone fractures, pseudoarthroses and the like with the use of ultrasound. An ultrasound transducer, in contact with the skin of the patient, transmits ultrasound pulses to the site of the bone defect. The nominal frequency of the ultrasound is 1.5 MHz, the width of each pulse varies between 10 and 2,000 microseconds, and the pulse repetition rate varies between 100 and 1000 Hz. The power level of the ultrasound is maintained below 100 milliwatts per square centimeter. It is stated therein that treatments which last about 20 minutes per day have been found to heal certain defects in less than two months.

Another method referred to in Duarte which has been employed in an attempt to accelerate healing is the application of direct current, on the order of 20 microamperes, at the site of a fracture. The cathode is usually applied at the site of the defect, whereas the anode is placed somewhere in the adjacent tissue or on the skin of the patient. Unfortunately, such arrangements are totally or partially invasive, which raises the concomitant possibility of infection. With non-invasive techniques, such as causing an externally generated electromagnetic field to pass through the fracture site to induce a current, precise alignment of the coils relative to the area to be treated is required, as well as treatment being required for 12 to 16 hours a day.

In the past, acoustic shock waves have been used to treat patients, but not in relation to bone. For example, shock wave treatments have been widely used to break up kidney stones to avoid invasion of the patient's body by instruments. Such treatments are described in publications such as U.S. Pat. No. 3,942,531 to Hoff et al. and *Extracorporeal Shock Wave Lithotripsy*, 1982, edited by Christian Chaussy and published by Karger AG of Basel, Switzerland. Generally, shock waves are generated exteriorly of the patient's body in a medium such as water and transmitted into the patient's body with suitable coupling to minimize energy absorption at the interface with the patient's skin. As pointed out in Chaussy, the shock waves (which differ from ultrasound wave inputs in that they have a very steep compression pressure rise front and little or no tension component) may travel through normal soft body tissue (except the lungs) at high pressure amplitudes without materially injuring the tissue.

As mentioned above, other interferences with the equilibrium between bone decomposition and bone building are osteopathies such as osteoporosis. Osteoporosis literally means "porous bone". While the outer form of the bones does not change unless there is a fracture, the bones have less substance and so are less dense. Osteoporosis is a common condition, affecting tens of millions of individuals around the world. For individuals over 45 years of age, approximately 70% of all fractures are related to osteoporosis.

In osteoporosis, bone mass decreases, causing bones to be more susceptible to fracture. A fall, blow, or lifting action that would not normally bruise or strain the average person can easily break one of more bones in someone with severe osteoporosis.

The spine, wrist and hip are the most common sites of osteoporosis-related fractures, although the disease is generalized, that is, it can affect any bone of the body. When the vertebrae are weakened, a simple action like bending forward to make a bed, or lifting a heavy pot roast out of the oven can be enough to cause a spinal compression fracture. These fractures often cause back pain, decreased height, and a humped back.

As a person grows during youth, bones are metabolically active, and calcium is deposited into bone faster than it is taken out. The deposition of calcium and phosphorus into bone peaks at about 35 years in men and women. At the time of peak bone mass, the bones are most dense and strong.

After a person's late thirties, calcium begins to be lost from bones faster than it is replaced, and bones become less dense. In addition, in general, as both women and men age, their bodies begin to absorb less calcium from food. In addition, particularly at the age of 40, several complex factors influence the quantity and quality of bone. These include: level of adult peak bone mass; rates of bone loss due to menopause and due to aging; certain systemic hormones (such as calcitriol, an active form of vitamin D; parathyroid hormone; and calcitonin); substances produced by the bones themselves; diet (especially calcium intake); intestinal and kidney function; and physical forces that act on the bone such as those caused by body weight and exercise.

Given the complexity of the factors that influence bone, there are believed to be many ways in which osteoporosis can develop. However, there appear to be at least two strong contributing factors which predominate: a drop in estrogen levels in women due to menopause and a chronically low intake of calcium.

Even in situations where a fracture of the bone has not occurred as a result of osteoporosis, osteoporosis may interfere with treatment of other conditions. For example, joint replacement therapies require relatively healthy bone to serve as support for the synthetic replacement. For example, in hip replacement operations, osteoporosis may preclude insertion of the shaft bearing the new ball in the femur because of decalcification.

One current method for recalcification of the femur prior to hip replacement surgery is to perform surgery to expose the femur and make multiple fractures in the bone to induce recalcification over a period of several weeks before conducting a second operation to effect hip replacement. Even when successful, it is not uncommon for erosion of bone to occur subsequent to replacement.

Similarly, where plates are applied to a bone to immobilize it while healing occurs, sufficient bone must be present to hold the plate in place.

Estrogen replacement therapy and increased calcium intake are currently commonly prescribed for osteoporosis. However, generally such treatments are designed to prevent rather than treat osteoprosis. A need continues to exist for drugs and techniques that can prevent osteoporosis as well as treat it after it has occurred.

SUMMARY OF THE INVENTION

The present invention is a method of inducing bone growth. The method comprises directing energy in the form of acoustic shock waves to a site where bone growth is desired, the amount of energy applied being sufficient to produce bleeding.

DETAILED DESCRIPTION OF PREFERRED EMBODIMENTS

Figure 1:
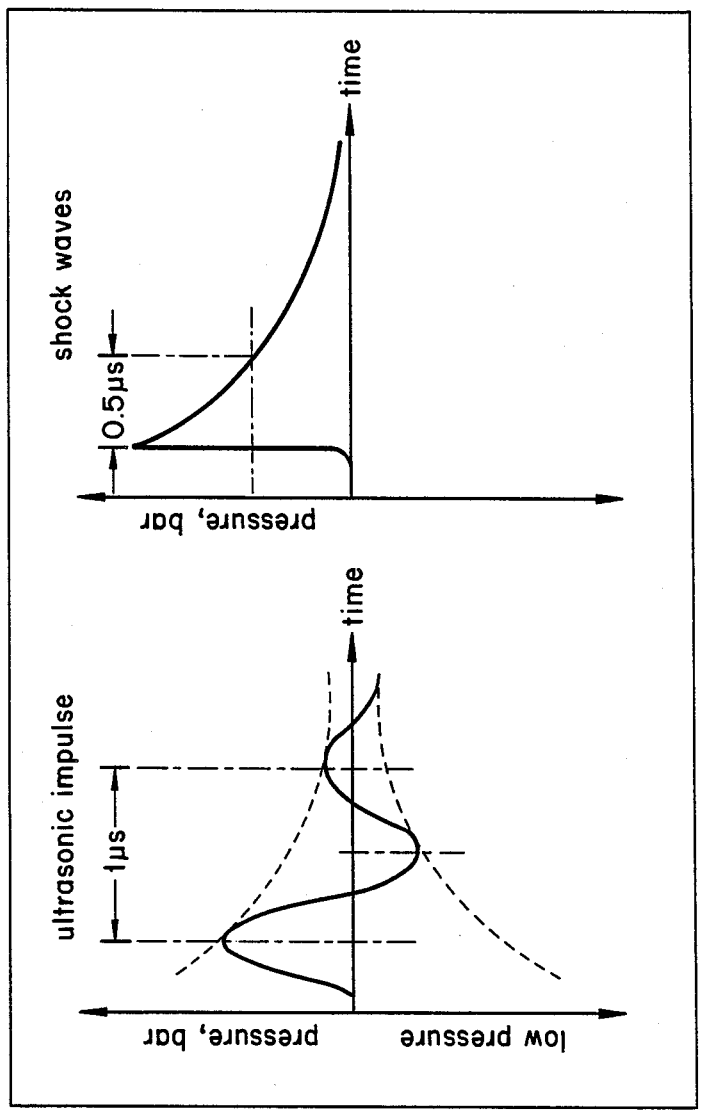

By the present invention, a method of inducing bone growth is provided which is noninvasive but results in a similar reaction by the body as if a fracture had occurred. On a microscopic level, it is believed that the application of acoustic shock waves probably does not lead to microfractures, but rather merely to a restriction of the microcompartments of the bone. It has been determined that a relatively high iron content is seen within two days after the application of acoustic shock waves, thereby indicating the presence of a hematoma, which as discussed above, is critical to the formation of new bone. Three weeks after treatment with acoustic shock waves, iron contents have generally returned to normal.

The nature of the shock waves utilized in the present invention will be explained with reference to FIG. 1 which depicts an idealized format characteristics of both an ultrasonic wave impulse which is not suitable for the practice of the present invention and an acoustic shock wave which is suitable. In each instance, the wave form is displayed in a pressure versus time diagram where pressure is indicated by the vertical direction and time is indicated by the horizontal direction. Pressures above ambient are located above the "time" axis and pressures below ambient are located below the "time" axis.

The ultrasound wave at the left of FIG. 1 is sinusoidal in nature in that the pressure rises regularly to a maximum value above ambient, falls regularly through ambient and on to a minimum value below ambient, and then rises regularly again. It will be understood that the portion of the curve above the "time" axis represent "compression" (shrinking) conditions in the medium in which the wave moves and the portion of the curve below the "time" axis represents "tension" (expanding) conditions in the medium.

The idealized shock wave at the right of FIG. 1 has a single pressure spike with very steep onset and a more gradual relaxation. Moreover, it has no "tension" component in that pressures throughout are above ambient.

Some parameters associated with the shock waves which are emphasized in practicing the invention will promote a more complete understanding. With regard to the steep compression wave front, a typical rise time (period from onset to peak) is less than about $10^{-7}$ seconds. The maximum pressure attained will be quite high, appropriate values being in the range of about 20 bar to about 2000 bar with values greater than 50 bar and preferably greater than 100 bar being favored in the absence of apparatus limitations or problems associated with the subject being subjected to the waves. The overall duration of the whole wave event can be expected to be on the order of $10^{-6}$ or less second, and the wave will have little or no "tensile" (pressure below ambient) component. In this latter regard, any "tensile" component should be less than 25%, and preferably less than 10%, of the maximum pressure amplitude, and any oscillation should be minimized.

The absence of extensive tension wave components in shock waves is important from the standpoint of undesired tissue damage in patients. While it is an intended result of the present invention initially to cause trauma within the designated bone site, it is important that the waves pass through the intervening soft tissue without substantial trauma. Tension wave conditions are tolerated less well than compression wave conditions, and pressures far below ambient tend to cause damage to tissue. Hence, these components should be minimized both in amplitude and extent where possible.

The frequencies represented in the two types of waves diagrammed in FIG. 1 also are significant with respect to the biological effects the waves produce. A shock wave may be considered as a delicate composition of longitudinal waves covering a very large frequency range. In contrast therapeutic ultrasound represents a more or less short wave train of ultrasonic waves. Due to the extremely short rise time, the shock wave is a unique means to realize high compression zones within the tissue without producing heat and cellular degradation. Ultrasonic waves of a comparable energy regime would definitely produce heat and cellular degradation, whereas shock waves have far less effect on the patient's body.

To further illustrate the differences between the use of shock waves in the present invention versus the use of pulsed ultrasound as recommended in Duarte, the following Table I is provided which lists various pertinent parameters:

TABLE I

| | Pulsed Ultrasound | Shock Waves |
| --- | --- | --- |
| intensity | 0.1 W/cm$^2$ | 300 kW/cm$^2$ |
| maximum pressure amplitude | 0.4 bar | 1 kbar |
| frequency | 1.5 MHz | 0.5 MHz (average frequency) |
| rise time | 170 ns | <50 ns |
| pulse length | 2–10 $\mu$s | ~6 $\mu$s |
| repetition rate | $10^2$–$10^3$ Hz | ~1 Hz |
| wavelength (H$_2$O) | 1 mm | ~3 mm (average wavelength) |
| energy density (H$_2$O) | 0.5 × $10^{-6}$ WS/cm$^2$ | 2 WS/cm$^2$ |

Several important points should be appreciated from the above. Initially, the very large differences in energy density and maximum pressure amplitude should be noted. Duarte provides a pulse length (i.e., time) of approximately the same duration as the present invention. However, because the intensity (i.e., power) is so much smaller, the energy density in the form of the maximum pressure amplitude in Duarte is extremely small compared to the present invention. Indeed, the process of Duarte would not produce the intrabone hematoma desired by the present invention.

Moreover, any attempt to modify Duarte to provide comparable energy using ultrasound would not be physiologically successful. Essentially, shock waves succeed by supplying high power in a short time, due to a rapid rise time to the maximum pressure amplitude. To obtain the same amount of energy from ultrasound, it would be necessary to supply relatively low power for a much longer time. The result of the longer time of application would be storage of energy in the tissue between the skin surface and the bone, with concomitant heating and tissue degradation.

It is only through the application of shock waves that the intrabone trauma desired by the present invention can be obtained. No other method of supplying energy can produce such trauma.

FIG. 2 shows a diagrammatic view of an apparatus setup for inducing bone growth within a patient's body by shock wave treatments. A shock wave source 32 and a patient 34 are positioned in a container 30 of water. Source 32 is a spark gap device driven by an electrical condenser which releases its energy in a very short time. Shock wave source 32 is driven by power supply 38. An arc arises between the electrodes of the spark gap device which vaporizes the water surrounding the arc's path, establishing a plasma-like state. The result is an explosion-like vaporization of the water which produces a shock wave that spreads out in a circular fashion.

With this embodiment, the shock wave source is arranged in the focus F1 of an ellipsoid of revolution 36. Shock waves emanating from the shock wave source are concentrated in the focus F2 where the bone to be treated is located. Since the impedance in the water bath is about the same as the speed of sound in body tissue, the illustrated arrangement advantageously couples the shock waves into the patient's body with little reflection of energy at the body-water interface and with little likelihood of injury to the patient, all in a manner well known to those skilled in the medical applications of shock waves.

The illustrated arrangement also permits safe relative movement between the shock wave source and parts of the patient's body so that the shock waves may be focused to the bone where the growth of new bone mass is desired.

Other physical arrangements are of course possible. For example, instead of using a water bath for the patient, it has been proposed to interpose a suitable diaphragm or membrane between the patient's skin and a water cushion in which shock waves are generated. With such arrangements, a flexible bellows can be used for coupling so that relative movements can be accomplished for focusing the shock waves as required.

Other systems for generating shock waves may of course be used if desired. It is known, for instance, that laser beam energy focused at the focal point F1 can produce an acoustical shock wave emanating from that point.

Other energy inputs (e.g., electromechanical sources and piezoelectric generators) and other focusing techniques (e.g., hemispheres, lenticular focusing by a lens or lens system) also are possible. An array of piezoelectric devices arranged on a spherical segment or concave support, and suitably driven to provide shock wave outputs, can provide shock waves which converge or focus at a point or zone spaced away from the support; and such an arrangement has been proposed for introducing shock waves into a patient's body.

It is important to distinguish between the induction of bone growth, i.e., causing bone growth to begin, versus stimulation, i.e., enhancing a process which is already occurring. Particularly, in the case of osteoporosis, no bone growth whatsoever would occur unless such is induced due to the application of acoustic shock waves. Moreover, in smooth fractures such as stress fractures, the low resulting pertubation results in minimal hematoma formation and essentially no formation of bone.

By the application of acoustic shock waves, new bone growth can be induced, thereby resulting in healing which would otherwise be delayed or would not occur. The present method can be used both in cases where new growth is desired as well as cases where the rate of repair is impaired for some reason.

Another potential use of the method of the present invention is the insertion of prosthesis without the use of cement. When cement fixation of an implant occurs, the inner two-thirds will not receive any antibiotic coverage since the inner two-thirds does not have nutrition or circulation. In addition, the thermal detrimental effect of the cement also contributes to the inoperability of antibiotics. Thus, antibiotics given after occlusion of the medullary circulation cannot be expected to give any protection to the two-thirds of the cortex regardless of how high a dose, i.e., piggyback or antibiotic chosen. Many times infection may appear a considerable period of time following cementing of the prosthesis because granulation will not occur until circulation has resumed. With the lack of circulation, granulation response plus crucial bone mass to produce callus may be delayed for years. Accordingly, a need has continued to exist for procedures which would allow cementless insertions of prostheses.

By the present invention, cementless prostheses insertion becomes a viable and sensitive alternative. The prosthesis is inserted in such a manner that sufficient room is left for circulation to allow granulation to occur and to insure that antibiotics can reach the implant surface area. Subsequent to implantation, acoustic shock waves would be applied to the area adjacent the prosthesis to induce the formation of bone, thereby anchoring the prosthesis firmly in place.

Another potential use for the method of the present invention is where a bone is improperly formed, thereby not performing proper function. For example, in conditions where the hip socket is not deep enough, focused application of acoustic shock waves can result in the formation of additional bone mass at the periphery of the socket, thereby remedying the previous condition. the same principle can be applied to any bone to reshape as desired.

Another condition which may be treated is to prevent the degenerative changes which occur during joint immobilization. As discussed above, one of the elements controlling the continued vitality of bone is the application of weight. When a joint is immobilized, and thus does not bear weight for a period of time, decalcification begins. By the application of acoustic shock waves, such degenerative changes can be prevented or at least minimized, thereby lessening the period of time necessary to achieve complete recovery.

Another advantage of the present invention over prior art methods is that a single treatment or a relatively small number of treatments are required, in contrast to the daily treatments involved in prior art methods which utilize ultrasound or electrical stimulation.

The number of acoustic shock waves necessary to induce bone growth will vary depending upon the age of the individual and the particular bone involved. For example, an older individual may need to have more stimulation applied to provide a sufficient level of induction. Considering the HM 3 shock wave generator system (Dornier Medizintecknik GmbH, Germering, Federal Republic of Germany), for example, a dose of 18–25 kV (corresponding to peak amplitude pressures of not less than 800 bar ($=8 \cdot 10^7$ Pa)) times 1500 acoustic shock waves in a single application will generally be effective for a bone such as a femur or iliac. For example, shock waves having a peak amplitude pressure of at least 800 bar ($8 \times 10^7$ Pa) and an intensity of about $10^5$ Watt/cm$^2$ can be employed. While lower voltages can be used, generally a minimum of 18 kV (corresponding to a focal peak amplitude pressure of approximately 1000 bar ($=10^8$ Pa) is necessary to induce bleeding and thereby produce hematomas which induce bone growth. Generally, a minimum of about 500 acoustic shock waves would be applied in a single application. In a preferred embodiment, at least 1000 shock waves having a peak amplitude pressure of at least 1000 bar are applied. In general, the application of acoustic shock waves show a necrosis of existing trabecula structures in the spongiosa treated, followed by the appearance of intraosseous hematoma and their subsequent transformation into vital trabecula. In addition, a propagation of inwardly directed compacta is observed.

In connection with osteoporosis, potential areas of application of acoustic shock waves are the spinal column, the end of the femur near the hip, and the wrist, since these are the areas most likely to fracture.

In order to further illustrate the present invention and the advantages thereof, the following specific example is given, it being understood that this example is intended only to be illustrative without serving as a limitation on the scope of the present invention.

EXAMPLE

To demonstrate the present invention, acoustic shock waves were applied to white New Zealand female rabbits. The left distal femur and the left iliac bone were treated with acoustic shock waves. The right distal femur and right iliac bone were used as controls. The animals were divided into three groups, one group was killed two days after application, the second group 14 days, and the third group 21 days after application. The left and right femur and left and right iliac bone were removed, shock frozen in liquid nitrogen and stored for analysis at $-80°$ C.

Chemical investigations were conducted in a manner described by Althoff et al, "Morphological Studies on the Epiphyseal Growth Plate Combined with Biochemical and X-ray Microprobe Analyses", *Histochemistry*, 74, pages 541-552 (1982). The investigations were effected topologically, i.e., the area of the femur directly exposed to the acoustic shock waves was examined separately from an area which was further removed from the same femur but not directly involved. Data obtained was compared with corresponding data from the untreated right control femur. The same procedure was followed for the iliac bones.

A commercially available lithotripter, the model HM3 available from Dornier, Munich, Federal Republic of Germany, was employed. 1500 impulses were applied at a generator voltage of either 25 kV or 20 kV. A necropsy examination was conducted on both the macroscopic and microscopic level to determine whether the shockwave had effects outside the area of application.

It was determined that petechiae appeared on the skin of each of the rabbits treated with acoustic shock waves, whereas hematoma only appeared in approximately half of the animals treated. Rectal bleeding was observed in all but one of the rabbits treated at 25 kV, whereas only approximately two-thirds of the rabbits in the group treated with a dose of 20 kV exhibited rectal bleeding. While a certain amount of bleeding in other areas was observed in a few individual cases, in general only those areas treated directly with acoustic shock waves were observed to have experienced substantial change.

In general, the application of acoustic shock waves appears to stimulate the body to react in the same way as it would to a fracture, but in a weakened manner. Soon after shockwave application, there are changes in bone metabolism which indicate a qualitatively altered bone. The calcium and phosphorus contents are lower than before application of shock waves, together with their molar ratios. The iron and copper concentrations are increased (with the higher iron content indicating the formation of hematomas). The concentrations of trace elements essential for bone metabolism, magnesium, nickel and aluminum, are higher. Thus, the body apparently reacts to the stimulus applied to it with deficiency states or with the provision of additional trace elements.

Within two days after shock wave application certain remarkable metabolic changes have appeared. A lowered activity of acid phosphatase and beta-glucuronidase are seen indicating a disturbance of the osteocyte and/or osteoclast metabolism, i.e., the bone decomposing activity is apparently decreased. Similarly, the proportion of extractable hexosamine and extractable phosphorus have decreased indicating bone metabolism.

In contrast, the osteoblasts appear to have experienced little reduction in activity since the values of alkaline phosphatase activity have not declined. Thus, no increase in bone has occurred at this point.

Only when damaged cells and possible necrotic areas are vascularized and are slowly restored, is an increase in the osteoblast and osteoclast activities to be expected. By fourteen days after shock wave treatment, a strong increase in alkaline phosphatase activity is observed, thereby indicating that bone building activity has increased.

Thus, approximately two weeks after the application of acoustic shock waves, the bone reacts with reorganization processes which correspond in many details to the various stages of osseogenesis in length, growth, and certain stages of osteoneogenesis following experimentally set osteotomy. Thus, the molar calcium/phosphorus ratio corresponds to the values, together with the decreasing manganese content, found in the reorganization region of the primary spongiosa to trabecular bones in length growth.

Moreover, from the measurements of the various concentrations, it can be seen that the acoustic shock waves lead not only to reactions in the treated parts, but also in surrounding bone regions in a similar manner. In view of the time dependent concentration variations following the application of acoustic shock waves, it would appear that there is an interaction resulting from various co-factors such a enzymes, either as activators or as inhibitors, depending on the functional state of the bone. Accordingly, treatment of selected sites in individuals suffering from osteoporosis may result in desirable systemic effects.

While the invention has been described in terms of various preferred embodiments, one skilled in the art will appreciate that various modifications, substitutions, omissions and changes may be made without departing from the spirit thereof. Accordingly, it is intended that the scope of the present invention be limited solely by the scope of the following claims.

What is claimed is:

1. A method of inducing bone growth in a mammal which comprises directing acoustic shock waves to a site where bone growth is desired, the shock waves applying an amount of pressure sufficient to produce bleeding at said site, said amount of pressure being sufficient to induce bone growth.

2. The method of claim 1 wherein the shock waves have a peak amplitude pressure of at least 800 bar ($8 \times 10^7$ Pa) and the intensity is about $10^5$ Watt/cm$^2$.

3. The method of claim 2 wherein at least 500 shock waves are applied.

4. The method of claim 3 wherein the shock waves have a peak amplitude pressure of at least 1000 bar.

5. The method of claim 4 wherein at least 1000 shock waves are applied..

6. A method of treating osteoporosis in a mammal which comprises directing acoustic shock waves to bones which have suffered decalcification, the shock waves applying an amount of pressure sufficient to produce bleeding in said bones, said amount of pressure being sufficient to induce bone growth.

7. The method of claim 6 wherein the shock waves have a peak amplitude pressure of at least 800 bar ($8 \times 10^7$ Pa) and the intensity is about $10^5$ Watt/cm$^2$.

8. The method of claim 7 wherein at least 500 shock waves are applied.

9. The method of claim 8 wherein the shock waves have a peak amplitude pressure of at least 1000 bar.

10. The method of claim 9 wherein at least 1000 shock waves are applied.

* * * * *